(12) United States Patent
Timm et al.

(10) Patent No.: US 6,723,110 B2
(45) Date of Patent: Apr. 20, 2004

(54) HIGH EFFICIENCY ULTRASONIC SURGICAL ASPIRATION TIP

(75) Inventors: Ed Timm, Wildwood, MO (US); Mike Auld, Chesterfield, MO (US)

(73) Assignee: Synergetics, Inc., St. Charles, MO (US)

( * ) Notice: Subject to any disclaimer, the term of this patent is extended or adjusted under 35 U.S.C. 154(b) by 0 days.

(21) Appl. No.: 10/122,754

(22) Filed: Apr. 15, 2002

(65) Prior Publication Data

US 2002/0156492 A1 Oct. 24, 2002

Related U.S. Application Data

(60) Provisional application No. 60/284,913, filed on Apr. 19, 2001.

(51) Int. Cl.[7] .............................................. A61B 17/32
(52) U.S. Cl. ........................ 606/169; 606/170; 600/471
(58) Field of Search ................................ 606/169, 184, 606/185; 600/461, 566, 437, 567, 464, 471; 604/22

(56) References Cited

U.S. PATENT DOCUMENTS

| | | | |
|---|---|---|---|
| 3,896,811 A | | 7/1975 | Storz |
| 4,493,694 A | | 1/1985 | Wuchinich |
| 4,515,583 A | | 5/1985 | Sorich |
| 4,516,398 A | | 5/1985 | Wuchinich |
| 4,526,571 A | | 7/1985 | Wuchinich |
| 4,634,419 A | | 1/1987 | Kreizman et al. |
| 4,750,488 A | | 6/1988 | Wuchinich et al. |
| 4,823,793 A | | 4/1989 | Angulo et al. |
| 4,869,715 A | * | 9/1989 | Sherburne ................... 604/22 |
| 5,417,654 A | | 5/1995 | Kelman |
| 5,811,909 A | | 9/1998 | Wuchinich |
| 6,086,369 A | | 7/2000 | Sharp et al. |

OTHER PUBLICATIONS

SONOPET—Ultrasonic Surgical Aspirator model UST–2001 brochure.
Coopervision Surgical—Brochure on Surgical tips.
Pfizer—Valley Lab—Brochure on CUSA 200 system.
Valley Lab—CUSA Excel 36 kHz ultrasonic handpiece brochure.
Valley Lab—CUSA Excel 23 kHz ultrasonic handpiece brochure.
CUSA—System 200 PMT handpiece brochure.
Pfizer—Valleylab—Valleylab Cusa Pak brochure.
CUSA—Excel Technical Brief.
CUSA—Excel Ultrasonic Surgical Aspirator brochure.
LigaSure—Vessel Sealing System brochure.
CUSA—Cusa CEM System brochure.
CUSA—MicroTip brochure.
CUSA—System 200 "The Cutting Edge of Surgery Without the Cutting Edge" brochure.
Valleylab—Cusa Pak Disposables instructions and parts description.

\* cited by examiner

*Primary Examiner*—Michael J. Milano
*Assistant Examiner*—D. Jacob Davis
(74) *Attorney, Agent, or Firm*—Kevin L. Klug

(57) ABSTRACT

A high efficiency ultrasonic surgical aspiration tip apparatus and accompanying method for surgical use. The apparatus has one or more substantially "V" or "U" shaped cuts in a contacting. The apparatus and method of use provides a cutting action at the contacting end when the tip is ultrasonically excited. The apparatus and method of use further provides a substantially uniform ultrasonic and aspiration field due to the positioning and shape of the substantially "V" or "U" shaped cuts. The aforesaid further allows a surgeon to position the ultrasonic generator handpiece at any rotational angle for provision of the benefits cited.

2 Claims, 12 Drawing Sheets

HIGH EFFICIENCY ULTRASONIC SURGICAL ASPIRATION TIP

This application claims priority of Provisional Patent Application No. 60/284,913, filed Apr. 19, 2001.

BACKGROUND OF THE INVENTION

The art of the present invention relates to ultrasonic surgical devices in general and more particularly to a high efficiency ultrasonic tip for use in neurosurgery and other surgical disciplines. The use of ultrasonic aspirators in neurosurgery is well understood and recognized in the field of neurosurgery. Ultrasonic aspiration provides for emulsification and in situ evacuation of intracranial tumors. In this way, retraction of eloquent brain is minimized, while disruption and removal of tissue is advanced.

Prior art ultrasonic aspirators typically utilize a tubular tip having a threaded connecting end and a contacting end. The threaded connecting end attaches to an ultrasonic generator handpiece which injects ultrasonic energy into the tip and further allows for aspiration through said tubular tip. Said energy causes said tubular tip to elastically elongate and retract along the tubular axis at a frequency corresponding to the ultrasonic excitation frequency of the ultrasonic generator. Often the contacting end of said prior art devices is best described as a planar cut perpendicular to the tubular axis of the tubular tip. In other words, the contacting end is simply a flat cut at the tube end which is again perpendicular with the lengthwise tubular axis of the tip.

Prior art ultrasonic aspirators for neurosurgery rely solely upon the phenomenon of cavitation to reduce tissue to its emulsified form. That is, the contacting end of said prior art extends and retracts up to 350 microns at a rate from 20 to 50 kilohertz, thereby producing an ultrasonic field which creates a low pressure cavitation zone at the contacting end. The resulting low-pressure zone at the tip of the aspirator causes cell wall collapse and release of intracellular fluid which creates an emulsate. Therafter, said emulsate is aspirated through said tubular tip via the action of an aspiration system connected inline with said ultrasonic generator handpiece and said tubular tip.

This prior art method of emulsification and aspiration is extremely safe, as it maintains some selectivity of destruction and limits disruption of tissues with low water mass. However, there are times when this selectivity becomes problematic. Fibrotic meningiomas and calcified tumors are minimally affected by the aforementioned cavitation phenomenon thereby dramatically increasing operative time or in some instances completely prohibiting the use of ultrasonic aspiration for their removal. Hence, the benefits of in situ evacuation are lost on these pathologies. Likewise, tumors previously treated with radiosurgery can often find themselves "welded" to surrounding pathology. (i.e. dura, bony prominences within the skull base, etc.) Again, the aforementioned limitations of ultrasonic aspiration apply.

The present art utilizes an ultrasonic field to produce the aforementioned cavitation along with a cutting action at the contacting end of the uniquely designed tubular tip. That is, the present art provides in situ evacuation of the aforementioned intracranial tumors. The aforesaid cutting is promoted at the ultrasonically excited contacting end when the contacting end is not perpendicular to the tubular axis of the tubular tip. In other words, since the ultrasonically excited contacting tip longitudinally extends up to 350 microns, a slicing or mechanical cutting action may be promoted when the contacting tip has an angle relative to the tubular axis. Unfortunately, a simple angle on the contacting end relative to the tubular axis does not promote efficient aspiration or an optimum ultrasonic field.

The present invention represents a tubular tip having a "V" or "U" shaped cut or notch within the contacting end which provides optimum slicing or cutting action while also maintaining asymmetrical handpiece operation, an optimum ultrasonic cavitation field, and optimum aspiration. That is, the present invention represents a tubular tip which is utilized in the aforementioned prior art ultrasonic generator handpiece and provides the traditional ultrasonic and aspiration benefits and allows a surgeon to use the ultrasonic handpiece in any rotational axis position. The tubular tip has a connecting end and a contacting end, yet the contacting end is uniquely shaped to provide the aforementioned cutting action. In a preferred embodiment, said contacting end contains a substantially "V" or "U" shaped cut which provides the desired cutting or slicing action along with a desirable locus for uniform aspiration and ultrasonic field generation. The base of the aforementioned "V" or "U" cut is placed opposite the contacting end, or towards to the connecting end.

Accordingly, it is an object of the present invention to provide a high efficiency ultrasonic surgical aspiration tip having a contacting end which promotes mechanical cutting and slicing of various tissues and other materials, including fibrotic meningiomas and calcified tumors.

Another object of the present invention is to provide a high efficiency ultrasonic surgical aspiration tip having a threaded end which functions with prior art ultrasonic generator handpieces, produces a substantially uniform optimum ultrasonic and aspiration field, and also provides the desired cavitation.

A further object of the present invention is to provide a high efficiency ultrasonic surgical aspiration tip which provides an asymmetrical ultrasonic generator handpiece operation while also promoting efficient and convenient aspiration.

SUMMARY OF THE INVENTION

To accomplish the foregoing and other objects of this invention there is provided a high efficiency ultrasonic surgical aspiration tip and method of using the same. The method and apparatus provide for a unique and desired cutting or slicing action while further providing the traditionally desired aspiration and ultrasonic field generation. In a preferred embodiment, the apparatus is claimed in conjunction with a conventional ultrasonic generator handpiece of a surgical aspirator and the method of use is claimed in conjunction with the action of surgical tissue and tumor removal.

As aforementioned, in its preferred embodiment, the present art represents a tubular tip having a connecting end, a contacting end, and a "V" or "U" shaped cut or notch within the contacting end which provides optimum slicing or cutting action while also maintaining asymmetrical handpiece operation, an optimum ultrasonic cavitation field, and optimum aspiration through the interior tube portion of the tip. In the preferred embodiment, the base of said "V" or "U" shape is positioned closer to the connecting end than the legs of the "U" or "V". That is, the tips of the legs of the "U" or "V" represent the tip of the contacting end and face away from the connecting end. In the preferred embodiment, the connecting end comprises a male threaded portion which mates with a female threaded portion on the ultrasonic generator handpiece. Said connecting end further comprises a shoulder, away from said connecting end and toward said contacting end, which seats upon and with the mating end of the acoustic horn of the ultrasonic generator handpiece of the aspirator. Alternative embodiments may utilize attachment methods at the connecting end other than threads. These include but are not limited to mating pinned portions, welding, sweated connections, soldered connections, brazed connections, mechanical quick disconnects, and ball and detent connections.

Alternative embodiments utilize variations of the "V" or "U" cut in the contacting end. That is, a first alternative embodiment contains multiple "V" or "U" cuts at the contacting end which form in combination a serrated cut at the contacting end. Further alternative embodiments embody an asymmetrical "V" or "U" shaped cut at the contacting end. That is, one leg of the "V" or "U" is shorter or longer than the other. Still further alternative embodiments provide honed or sharpened edges on said contacting end to further the aforementioned cutting action.

In all of the aforementioned preferred and alternative embodiments of the present art a uniform and symmetric ultrasonic field is generated substantially near the contacting end and in line with the tubular axis of the tip. This desirable feature is not present in prior art devices which provide for or offer cutting action. That is, prior art devices have provided only a single or single compound angular cut on the contacting tip which does not provide a uniform and symmetric ultrasonic field at the contacting tip. That is, the prior art cut on the contacting end is asymmetrical, thereby limiting the ultrasonic energy which is transmitted to the fluid, tissue, or tumor in which it is embedded and further creating an asymmetric ultrasonic field in said medium. An asymmetric field forces the user to rotate the ultrasonic generator handpiece to place the ultrasonic field or cavitation at the desired location since the ultrasonic field does not radiate in a uniform or half-sphere isotropic manner from contacting end.

The preferred and alternative embodiments of the present art also provide the desirable optimum aspiration at the contacting end. Since the ultrasonic handpiece is substantially tubular in nature, a surgeon typically desires to utilize the ultrasonic handpiece without concern as to rotational position about the tubular axis. This is not possible with prior art tips which provide for a cutting action. Since the present art contacting end maintains a substantially planar front at the contacting end, aspiration and field generation occurs primarily inline with the tubular axis. This again, allows the user to asymmetrically position the ultrasonic generator handpiece while maintaining effective aspiration and ultrasonic cavitation effects. In toto, the present art maintains all of the prior art benefits of optimum placement and generation of the ultrasonic field and optimum asymmetrical aspiration while providing enhanced mechanical cutting action.

The present art tubular tips may be manufactured from a variety of materials which provide the desired modulus of elasticity and a sufficiently high elastic limit to withstand the transmitted ultrasonic energy. Materials include but are not limited to metals and their alloys of steel, stainless steel, titanium, and super-elastic nickel titanium. Further manufacturing materials include ceramics, composites, and plastics. The method of manufacturing the present art with the "V" or "U" cuts include but are not limited to traditional machining methods or non-mechanical machining methods such as laser cutting and electrical discharge machining (EDM).

The art of the present invention as contemplated is effective in the in situ evacuation of intracranial tumors. However, it is also capable of in situ evacuation of intervertebral disc material, thereby facilitating a minimally traumatic discectomy, and further use in ophthalmic ultrasonic surgery. It is also specifically contemplated that the present device could be used in general endoscopic surgery, including but not limited to, surgery of the colorectal tract, biliary system, thoracic cavity, and other pathologies not mentioned. A variant of this device could further be utilized for intravitreal fragmentation of dislocated crystalline lenses.

In use, the surgeon or assistant, first installs the tip within the mating end of the acoustic horn of the ultrasonic generator handpiece. In the preferred embodiment, this is by screwing the tip into the mating end and applying the proper torque. Once installed, the surgeon may, if desired or necessary for the surgery, place an irrigation sleeve or flue around said tip aft of said contacting end before the operation begins. (The irrigation sleeve allows the handpiece to provide irrigation fluid to the surgical site through the ultrasonic handpiece.) During the surgical procedure, the surgeon places the contacting end onto or near the tissue or tumor which he or she desires to remove. Once placed, the surgeon then energizes the ultrasonic generator handpiece and the vacuum aspiration system if desired. The ultrasonic energy transmitted to the contacting end then creates a uniform ultrasonic field relative to the tubular axis of the tip. This field is of such high frequency and amplitude that the liquid or tissue surrounding it cavitates or breaks down. This allows for removal of said material through the interior tube portion of said tip via the aforesaid vacuum aspiration.

BRIEF DESCRIPTION OF THE DRAWINGS

Numerous other objects, features and advantages of the invention should now become apparent upon a reading of the following detailed description taken in conjunction with the accompanying drawings, in which.

DETAILED DESCRIPTION

Figure 1:
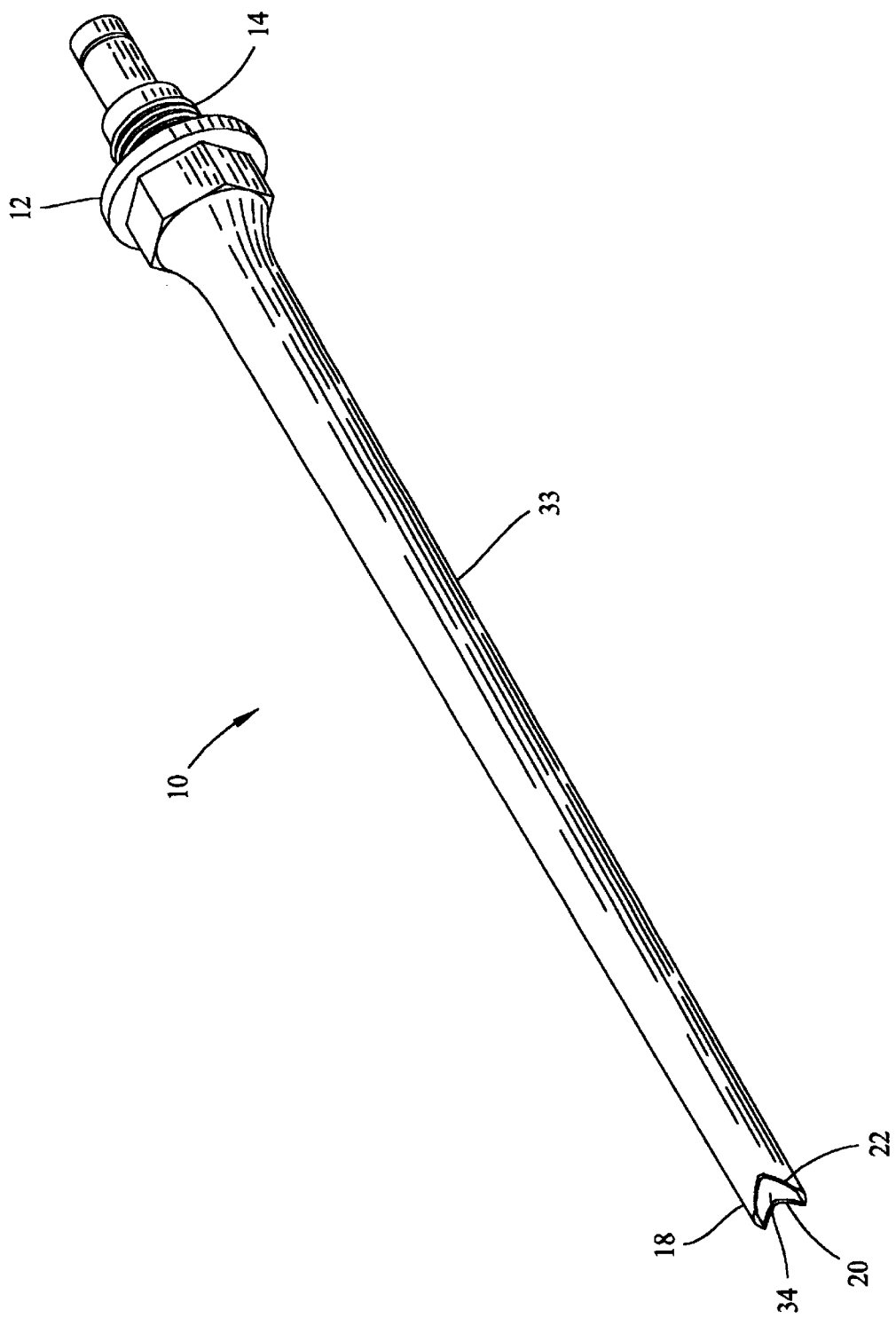
FIG. 1 is a perspective view of the high efficiency ultrasonic tip of the present art showing the substantially "V" or "U" shaped cut.
Figure 2:
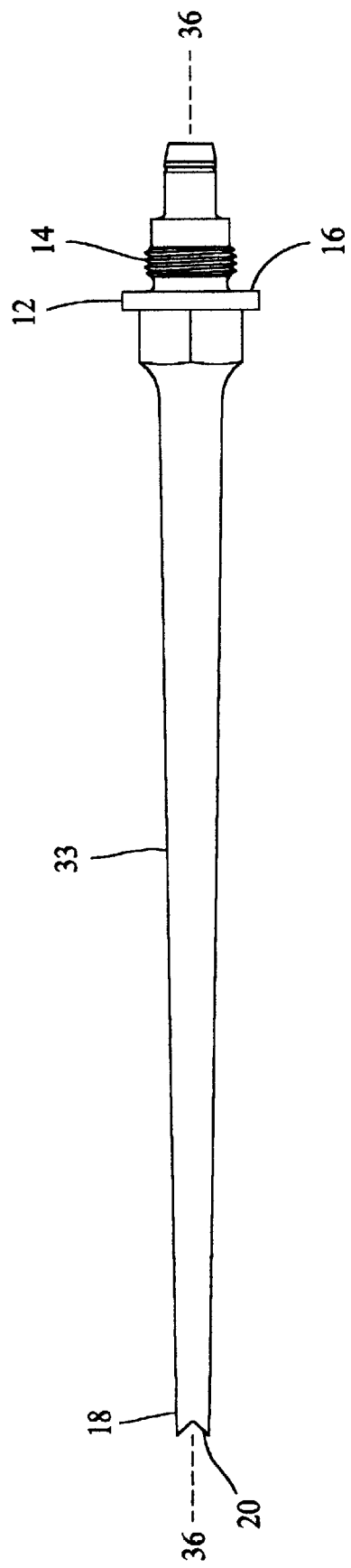
FIG. 2 is a plan view of a preferred embodiment of the high efficiency ultrasonic tip showing the connecting end and the contacting end along with the substantially "V" or "U" shaped cut.
Figure 3:
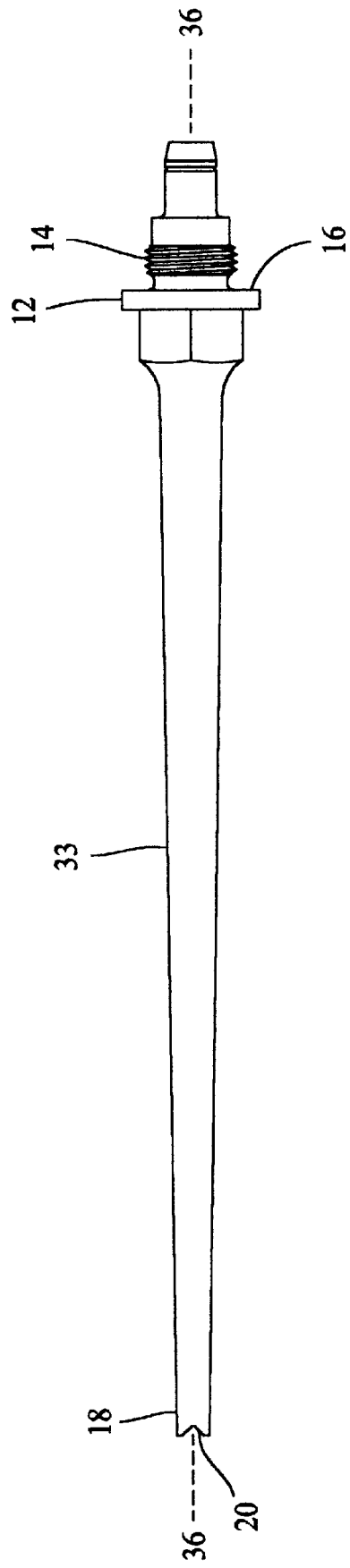
FIG. 3 is a plan view of an alternate embodiment of the high efficiency ultrasonic tip showing the connecting end and the contacting end along with the substantially "V" or "U" shaped cut.
Figure 4:
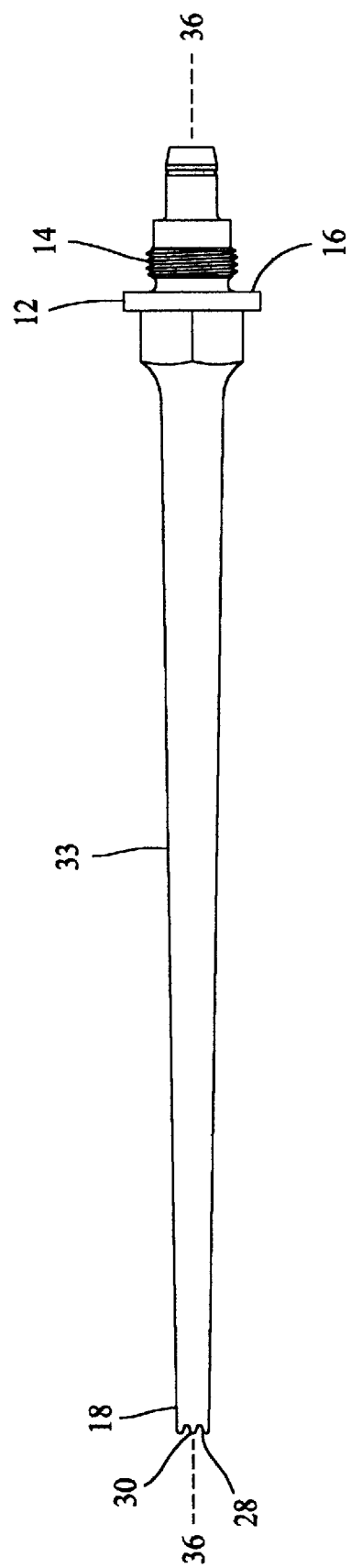
FIG. 4 is a plan view of an alternate embodiment of the high efficiency ultrasonic tip showing "V" or "U" cuts at the contacting end which form in combination a serrated cut at the contacting end.
Figure 5:
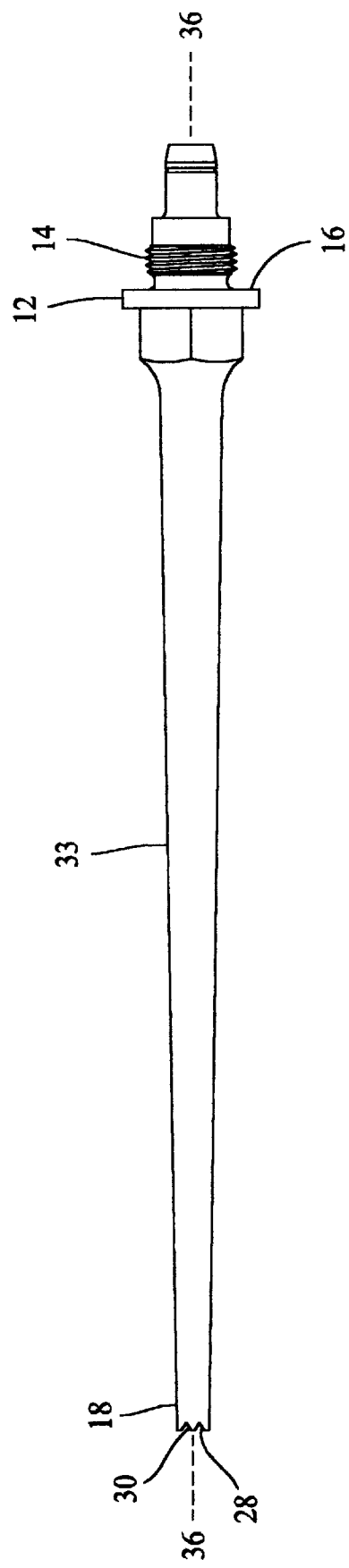
FIG. 5 is a plan view of a further alternative embodiment of the high efficiency ultrasonic tip showing "V" or "U" cuts at the contacting end which form in combination a serrated cut at the contacting end.
Figure 6:
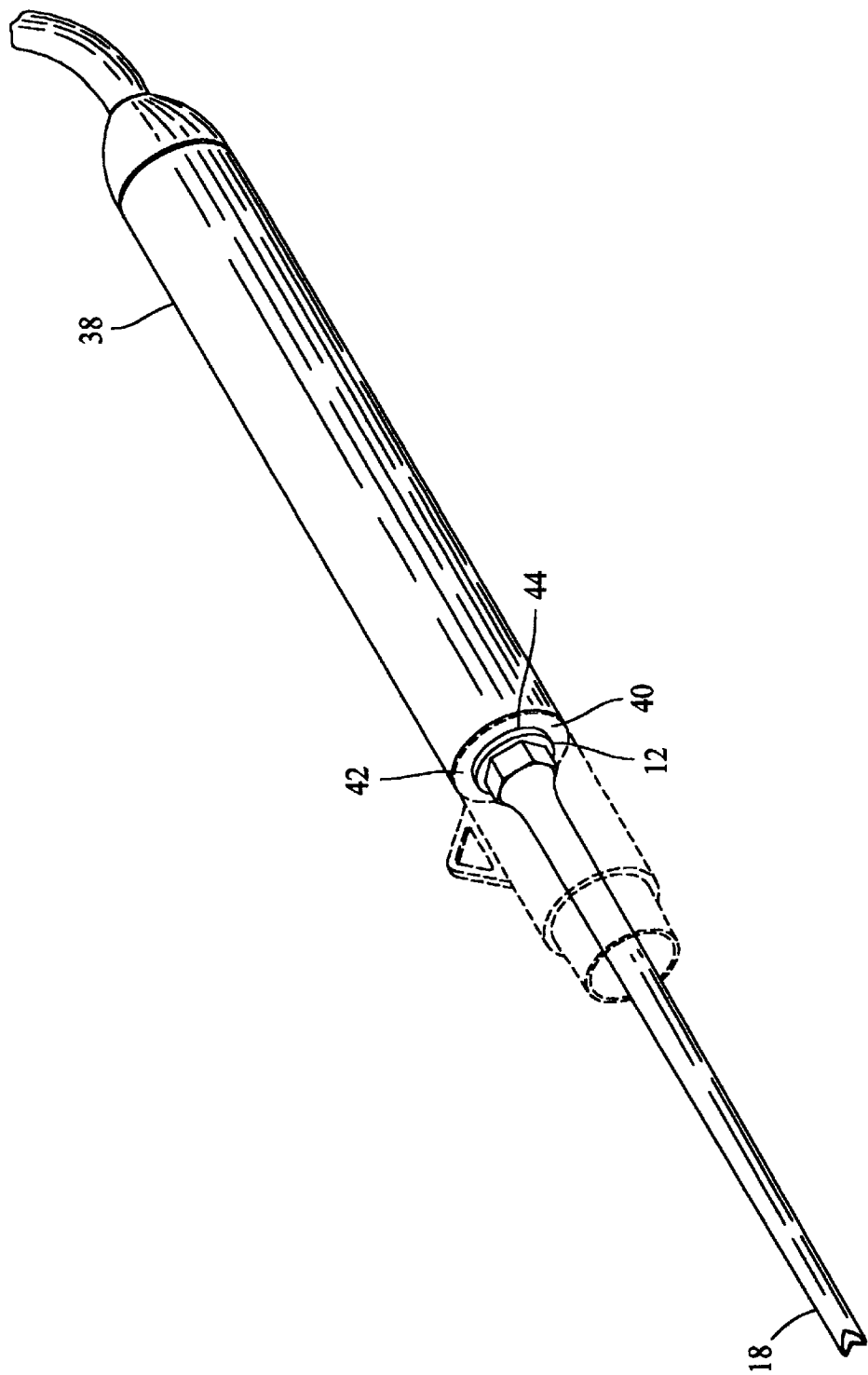
FIG. 6 is a perspective view of a preferred embodiment mounted upon a ultrasonic generator handpiece aspirator with the nosecone portion of the handpiece shown in phantom.
Figure 7:
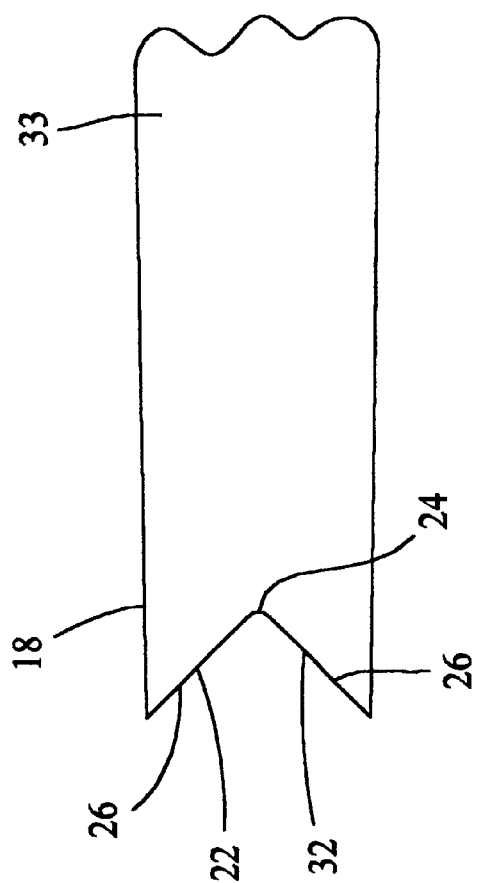
FIG. 7 is an exploded view of the contacting end of FIG. 2.
Figure 8:
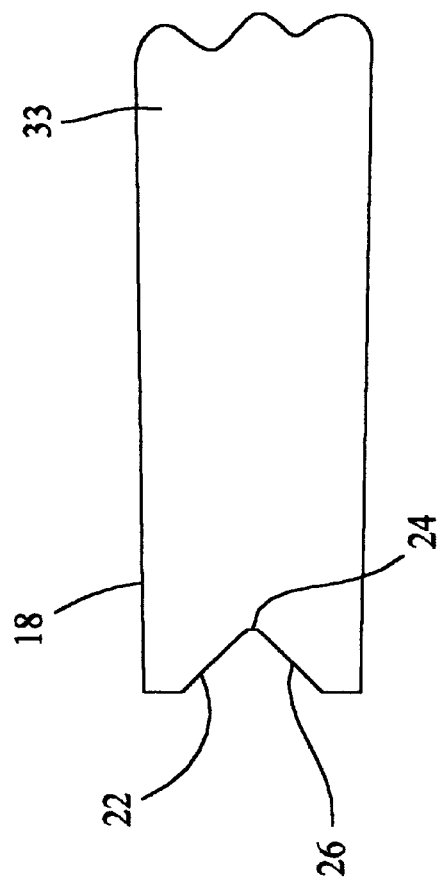
FIG. 8 is an exploded view of the contacting end of FIG. 3.
Figure 9:
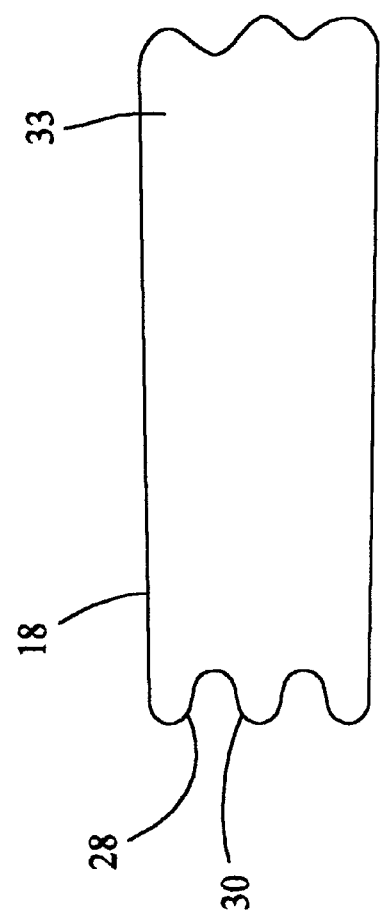
FIG. 9 is an exploded view of the contacting end of FIG. 4.
Figure 10:
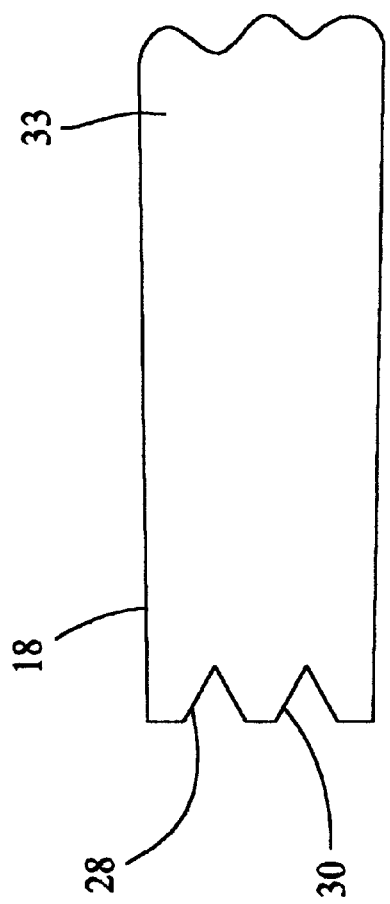
FIG. 10 is an exploded view of the contacting end of FIG. 5.
Figure 11:
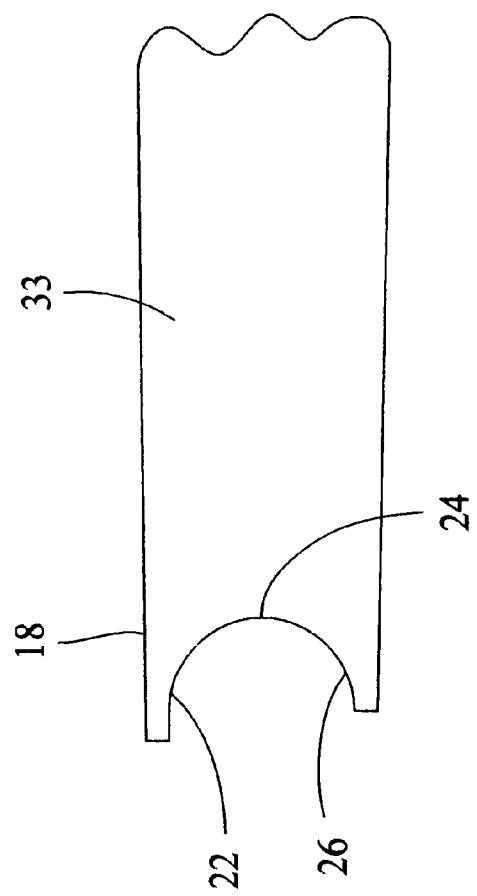
FIG. 11 is an exploded view of a contacting end showing two of the legs of the one or more substantially "U" shaped cuts of a different length.
Figure 12:
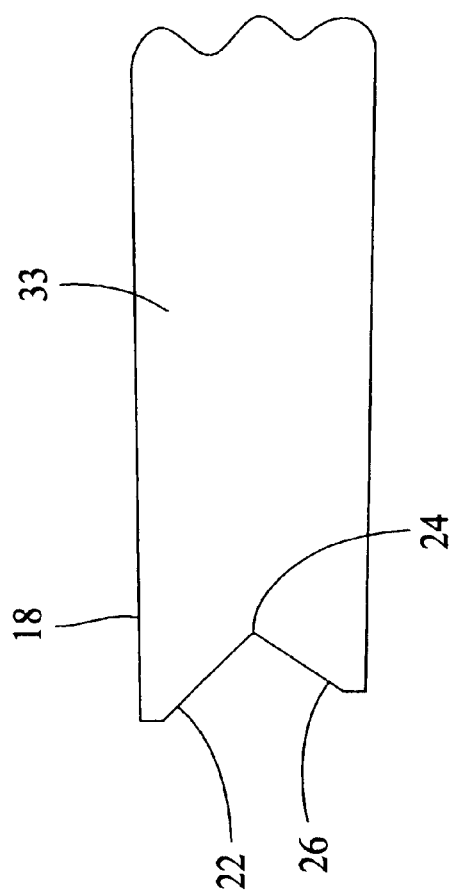
FIG. 12 is another exploded view of a contacting end showing two of the legs of the one or more substantially "V" shaped cuts of a different length.

Referring now to the drawings, there is shown in FIGS. 1, 2, 6, & 7 a preferred embodiment of a high efficiency ultrasonic surgical aspiration tip 10 and in FIGS. 3–5 & 8–10 alternative embodiments of the same. The high efficiency ultrasonic surgical aspiration tip 10 is particularly adapted to provide cutting action when ultrasonically excited with an ultrasonic generator handpiece 38 while further providing the desired symmetric and uniform ultrasonic field and aspiration relative to the tubular axis 36 of the tip 10.

The drawings show the apparatus comprising a connecting end 12 having a threaded portion 14 and a shoulder 16, a tube portion 33 having a tube axis 36 and an interior tube portion 34, and a contacting end 18 having a notch 20 with one or more symmetrical "V" or "U" shaped cuts 22, all of which function in conjunction with conventional ultrasonic generator handpieces 38. The tube portion 33 connects between said connecting end 12 and said contacting end 18.

In its preferred embodiment, the present art represents a tubular tip 10 having a connecting end 12, a contacting end 18, and a "V" or "U" shaped 22 cut or notch 20 within the contacting end 18 which provides optimum slicing or cutting action while also maintaining asymmetrical handpiece 38 operation, an optimum ultrasonic cavitation field, and optimum aspiration through the interior tube portion 34 of the tip 10. Asymmetrical handpiece 38 operation is further defined as utilization of the ultrasonic aspiration handpiece 38 without concern as to the rotational position of the handpiece 38 along its axis or the tubular axis 36 of the tip 10. That is, the surgeon need not rotate the handpiece 38 in order to align the cutting edges 32, ultrasonic field, or locus of aspiration with the evacuable tissue or tumor.

In the preferred embodiment, the base 24 of said "V" or "U" shape 22 is positioned closer to the connecting end than the legs 26 of the "U" or "V" 22 and is cut completely across the tube portion 33 symmetrically with the tubular axis 36. That is, the tips of the legs 26 of the "U" or "V" 22 represent the distal end of the contacting end 12 and face away from the connecting end 12. In the preferred embodiment, the connecting end 12 comprises a male threaded portion 14 which mates with a female threaded portion 44 of the ultrasonic generator handpiece 38. Said connecting end 18 further comprises a shoulder 16, away from said connecting end 12 and toward said contacting end 18, which seats upon and with the mating end 42 of the acoustic horn 40 of the ultrasonic generator handpiece 38 of the aspirator. As aforesaid, alternative embodiments may utilize attachment methods at the connecting end 12 other than threads, provided that said connection is of such intimate nature that the ultrasonic energy may transmit from said handpiece 38 into said tip 10. The connecting end 12 may further have one or more flat surfaces on its circumference which facilitate tool engagement for rotating and applying torque during attachment with said ultrasonic generator handpiece 38.

Alternate embodiments utilize variations of the "V" or "U" cut 22 as a notch 20 in the contacting end 18. That is, a first alternative embodiment contains multiple "V" or "U" cuts 28 at the contacting end 18 which form in combination a serrated cut 30 at the contacting end 18. Moreover, the multiple cuts may be positioned around the circumference of said contacting end 18 or may be completely through said contacting end 18. Further alternative embodiments embody an asymmetrical "V" or "U" shaped cut at the contacting end 18. That is, one leg of the "V" or "U" is shorter or longer than the other. Still further alternative embodiments provide honed or sharpened edges 32 on said contacting end 18 to further the aforementioned cutting action.

In all of the aforementioned preferred and alternative embodiments of the present art a uniform and symmetric ultrasonic field is generated substantially near the contacting end 18 and in line with the tubular axis 36 of the tip 10. The preferred and alternative embodiments of the present art also provide the desirable optimum aspiration at the contacting end 18. As aforesaid, since the ultrasonic handpiece 38 is substantially tubular in nature, a surgeon typically desires to utilize the ultrasonic handpiece 38 without concern for rotational position of said handpiece 38. Since the present art contacting end 18 maintains a substantially planar front at the contacting end 18, aspiration occurs primarily inline with the tubular axis 36. This again, allows the user to asymmetrically position the ultrasonic generator handpiece 38 while maintaining effective aspiration. Thus, the present art maintains all of the prior art benefits of optimum placement and generation of the ultrasonic field and optimum asymmetrical aspiration while providing enhanced mechanical cutting action.

In use, the surgeon or assistant, first installs the tip 10 within the mating end 42 of the acoustic horn 40 of the ultrasonic generator handpiece 38. In the preferred embodiment, this is by screwing the tip 10 connecting end 12 into the mating end 42 and applying the proper torque. Once installed, the surgeon may, if desired or necessary for the surgery, place an irrigation sleeve or flue around said tip. The sleeve is typically placed aft of said contacting end 18 with said contacting end 18 extending therefrom and provides a continuous pathway for delivery of irrigation fluid. During the surgical procedure, the surgeon places the connecting end 18 onto or near the tissue or tumor which he or she desires to remove. Once placed, the surgeon then energizes the ultrasonic generator handpiece 38 and the vacuum aspiration system if desired. The ultrasonic energy transmitted to the contacting end 18 creates a uniform ultrasonic field relative to the tubular axis 36 of the tip 10. This field is of such high frequency and amplitude that the liquid, tissue, or material surrounding it cavitates or breaks down. This allows for removal of said material through the interior tube portion 34 of said tip 10 via the aforesaid vacuum aspiration. If the tissue or material is attached to a structure or unaffected by the ultrasonic field, the surgeon places one or more of the edges 32 of said contacting end 18 onto the tissue or material and allows the ultrasonic displacement and movement of the contacting end 18 to physically cut said tissue or material. Again, the surgeon then evacuates the cut material through the interior tube portion 34 of the tip 10.

From the foregoing description, those skilled in the art will appreciate that all objects of the present invention are realized. A high efficiency ultrasonic surgical aspiration tip apparatus and an accompanying method of use has been shown and described. The apparatus of this invention is able to provide cutting action with any handpiece rotation positioning while further providing a uniform ultrasonic field and uniform aspiration.

Having described the invention in detail, those skilled in the art will appreciate that modifications may be made of the invention without departing from its spirit. Therefore, it is not intended that the scope of the invention be limited to the specific embodiments illustrated and described. Rather it is intended that the scope of this invention be determined by the appended claims and their equivalents.

What is claimed is:

1. A high efficiency ultrasonic surgical aspiration tip in combination with an ultrasonic generator comprising:

an ultrasonic generator handpiece having a mating end; and a tip having a connecting end, a contacting end, and a tubular portion between said connecting end and said contacting end, said tube portion having an interior tube portion and a tubular axis from said connecting end to said contacting end, said connecting end having means to connect and mate with said mating end of said ultrasonic generator handpiece, said contacting end having one or more substantially "V" or "U" shaped cuts, each having a base and legs, said "V" or "U" shaped cuts positioned onto said tube portion of said contacting end with the base of said "V" or "U" shape positioned closer to said connecting end than said legs of said "V" or "U" shaped cuts, whereby said "V" or "U" shaped cuts provide symmetric cutting action relative to said tubular axis when said tip is ultrasonically excited by said ultrasonic generator handpiece while further providing substantially symmetric ultrasonic field generation and aspiration relative to said tubular axis; and two or more of said legs of said one or more substantially "V" or "U" shaped cuts are of different length.

2. The high efficiency ultrasonic surgical aspiration tip in combination with an ultrasonic generator as set forth in claim 1 whereby:

said means to connect and mate with said mating end of said ultrasonic generator handpiece comprises a threaded portion and a shoulder on said connecting end and a female threaded portion within said mating end of said handpiece, whereby said threaded portion of said connecting end mates with said female threaded portion of said handpiece and said shoulder seats onto said mating end.

* * * * *